United States Patent [19]
Traina et al.

[11] Patent Number: 5,751,423
[45] Date of Patent: May 12, 1998

[54] OPACITY AND FORWARD SCATTERING MONITOR USING BEAM-STEERED SOLID-STATE LIGHT SOURCE

[75] Inventors: John E. Traina, Glenshaw; Richard Myers, Gibsonia; Edward A. Smierciak, Pittsburgh, all of Pa.

[73] Assignee: United Sciences, Inc., Gibsonia, Pa.

[21] Appl. No.: 761,127

[22] Filed: Dec. 6, 1996

[51] Int. Cl.⁶ .................................................. G01N 21/00
[52] U.S. Cl. .......................... 356/338; 356/440; 356/343; 250/574; 250/576
[58] Field of Search ............................. 356/336, 338, 356/343, 440; 250/574, 576, 436–439

[56] References Cited

U.S. PATENT DOCUMENTS

| | | | |
|---|---|---|---|
| 3,526,460 | 9/1970 | Webb | 356/343 |
| 3,915,572 | 10/1975 | Orloff | 386/343 |
| 4,221,485 | 9/1980 | Schulze | 356/338 |
| 4,541,719 | 9/1985 | Wyatt | 356/343 |
| 4,577,964 | 3/1986 | Hansen, Jr. | 356/338 |
| 4,791,427 | 12/1988 | Raber et al. | 343/754 |
| 5,132,548 | 7/1992 | Borden et al. | 356/336 |
| 5,173,958 | 12/1992 | Folsom et al. | 359/835 |
| 5,565,984 | 10/1996 | Girvin | 356/338 |

*Primary Examiner*—David C. Nelms
*Assistant Examiner*—Jason D. Vierra-Eisenberg
*Attorney, Agent, or Firm*—Buchanan Ingersoll, P.C.

[57] ABSTRACT

An improved transmissometer/particulate monitor of the type which has an optical assembly containing a solid state light source preferably a solid-state laser. The light source emits a collimated beam that is split, part of which is focused onto a reference detector that monitors the intensity of the light source, while the other part is directed to a beam-steering apparatus that causes the beam to accurately pass through a gaseous sample to a desired location such as a retro-reflector. A position-sensing detector is used in a closed-loop manner to control the beam-steering apparatus. The ratio of the total energy of the detected light beam, relative to the reference detector output, is used to determine the opacity of the gaseous sample or to provide a basis for correlation to particulate loading of the sample or both. The correlation to particulate loading is enhanced by a feature of the invention which measures the angular distribution of forward-scattered light to provide information as to the particle size distribution of the particulates.

19 Claims, 13 Drawing Sheets

OPACITY AND FORWARD SCATTERING MONITOR USING BEAM-STEERED SOLID-STATE LIGHT SOURCE

FIELD OF THE INVENTION

This invention generally relates to transmissometers of the type wherein the particulate concentration, optical transmission or opacity of a gaseous sample is measured as a function of the attenuation of a light beam passed through the sample and to light-scattering nephelometer instruments used to measure particulate concentration and size. Such devices are used for measuring particulate concentration, optical transmission, optical density and/or opacity of stacks or ducts which contain the gases resulting from burning fossil fuel, or process gases which contain particulates from industrial processes.

DESCRIPTION OF THE PRIOR ART

The federal government of the United States has set limits as to the amount of particulates and other pollutants that an electric utility or other business may emit into the air. In addition, there are limitations on visible emissions, also known as opacity. Typically these emissions are determined from measurements of the stack gasses as they flow through the stack. Opacity monitors, which are also called transmissometers, have been used as correlation devices to monitor the mass concentration of dust and other particulates passing through a stack or other conduit. Opacity is determined by passing a light beam through the stack gasses and determining the difference between the intensity of the original light beam and the intensity of the light which strikes a detector after having passed across the stack. In single pass monitors the detector is placed on the stack wall opposite the light source. In double pass systems a retro-reflector is located on the stack wall opposite the light source and reflects the light back through the stack to a detector positioned near the light source.

Most of the transmissometers of the prior art for stacks and ducts use an incandescent lamp as the optical source. This posed a number of shortcomings which are described in the U.S. Pat. No. 4,937,461, which discloses the use of a solid-state light source that emits light beams having a wavelength between 500 and 600 nanometers as the optical source. In recent years, the companies Land Combustion, Sick Optic Electronic, Codel, and Phoenix Instruments have all sold opacity monitors that use solid-state lamp technology. All of these prior art opacity monitors, whether using incandescent or solid-state lamps, require large mounting ports on the stack. The reason for this is related to the need to maintain alignment of the projected beam onto the retro-reflector on the other side of the stack or duct. Such systems are prone to alignment shifts due to thermal expansion and contraction of the stack and the hardware holding the light source, detector and retro-reflector. The mounting ports which hold these monitors on a stack must be large enough to allow for alignment tolerances. However, the mounting ports must be continuously purged with clean air, for the dual purposes of protecting the apparatus and avoiding blockage with particulate deposits. The large amount of purge air required by these large mounting pipes requires the use of large and expensive air blowers which in turn must be fitted with air filters to remove dust from the ambient air. Periodic replacement of these filters, cleaning of optical surfaces that have been fouled by imperfectly filtered purge air, condensation due to humidity in the purge air, and equipment damage from purge blower failure, constitute most of the maintenance associated with transmissometers. The preferable solution to all these problems would be to use dry, filtered instrument air, such as is commonly available at sites where transmissometers are used. However, the large amount, typically 20-60 cubic feet per minute, of purge air that is required to clean the large mounting ports prohibits this option.

Another family of transrissometers which use either solid-state lasers or helium-neon gas lasers has been sold by MIP and KVB. These instruments are single-pass transmissometers wherein the laser source is projected into one side of a stack or duct and a detector is located at the opposite side. One of the useful features of this device is that, because the laser beam is both intense and narrow, the instrument can be affixed to a stack or duct using small mounting ports, which in turn requires the use of less purge air to keep the ports free of particulate material from the gas stream being monitored. This permits the use of instrument air supplies which are commonly available at the job-site, rather than expensive blowers and the attendant maintenance of air filters. An additional advantage is that because laser beams are highly directional, a laser-based system can, in principle, be used over long measurement paths that would be difficult using less intense solid-state sources such as LEDs that diverge. However, this approach of using a narrow laser beam poses a severe difficulty inasmuch as the beam must be kept aligned onto the detector. For instance, if the laser beam is 0.25" in diameter and must be kept onto the active area of a detector that is 2" in diameter and 40 feet away from the laser source, the required alignment tolerance is ±0.15 degrees. This is not achievable in a cost-effective manner in many applications. A second disadvantage with this prior design is that it is a single-pass approach, requiring electronics on both sides of the stack or duct being monitored. Finally, the helium-neon laser generates large amounts of heat, is not rugged, is short-lived, and is expensive to replace.

A disadvantage common to all of the prior art involves the issue of calibration checks. The United States Environmental Protection Agency (EPA) requires that an opacity monitor that is being used to demonstrate compliance with visible emission standards be equipped with a mechanism that can be used to simulate a condition of zero particulate or zero opacity, and a condition equivalent to a predetermined upscale opacity or particulate concentration. These must be performed, at a minimum, once every 24 hours. Even when the transmissometer is not being used for EPA compliance, the user prefers to have this feature as a part of the system. The prior art typically achieves the zero condition by interposing into the projected light beam a reflective surface which simulates the effect of the retro-reflector under clear stack conditions. An upscale condition is simulated by interposing an optical filter between the sensing optics and the zero simulation mirror. In the prior art, implementation of this calibration check typically requires the use of additional mechanical moving parts such as solenoids, motors, bearings, and electrical relays.

A related disadvantage of the prior method of performing a zero and upscale calibration check is that, when the measurement pathlength of a transmissometer is changed, the gain factors of the instrument need to be adjusted. This, in turn, requires changing the zero surface such that the optical energy reflected by the zero device is now equivalent to the cross-stack distance at the new calibration distance. This is most often accomplished by manual adjustment of an iris that alters the cross section of the zero reflective surface.

Another disadvantage of all the prior art is that, since maintenance of alignment of the projected beam onto the retro-reflector is necessary to an accurate measurement, rigid and accurate mounting pipes are required. However, in many applications, the desired installation location is on the sides of metal stacks and ductwork which are not mechanically rigid. A significant part of the expense of installing this kind of equipment is associated with adding stiffeners, braces, and the like to existing stacks and ductwork in order to maintain alignment.

In addition to the zero and upscale check, the EPA standard for visible emissions monitoring requires a linearity check whereby two additional optical filters, corresponding to two additional upscale opacity values, are inserted into the measurement path. This is required to be done on a periodic basis, such as on the calendar quarter, and/or following repair or recalibration of the instrument. In most of the prior art systems, this must be done manually.

The most common use of transmissometer technology outside of the United States is for monitoring particulate concentration (e.g., milligrams of particulate per cubic meter of gas). It is obvious that when the particulate concentration increases in a conduit, with no changes in particulate composition, density, or size distribution, the attenuation of the beam of light passing through the conduit, and hence the opacity, will increase. However, in many cases, the causal factors that change the particulate concentration also change other particulate properties, most notably the size distribution. In typical smokestacks, for a fixed milligram per cubic meter concentration, the optical attenuation is inversely proportional to the average particle size. It follows that, if a transmissometer is being used for correlation to particulate concentration, even an approximate measurement of particle size can provide significant improvement in the accuracy of the calculation of concentration.

Consequently, there exists a need for a transmissometer which uses a narrow-beam solid-state light source with an automated means to sense the projected angle of the beam and maintain the alignment of the beam onto a retro-reflector. The system should be able to perform a zero calibration check and up to three upscale calibration points without the need for additional moving parts. In addition, for those cases in which a transmissometer is being used for correlation to particulate concentration, a means of determining particle size distribution is needed to correct the opacity-to-concentration correlation function.

SUMMARY OF THE INVENTION

We provide an opacity and forward scattering monitor containing a steerable, solid state light source which requires low power, is light and rugged, gives off low heat, has long life and can be directly modulated and run on reduced-duty cycling. This light source is collimated into a narrow axial beam and is dynamically steered so as to maintain alignment while overfilling a small retro-reflector. This configuration permits use of mounting pipes of typically 1.5" (3.8 cm.), as compared to 3.5" (8.9 cm.) to 6" (15.2 cm.) pipes required by the prior art. Since the volumetric flow required to purge a pipe goes as the square of the diameter, our monitor requires only 5 to 10 cubic feet per minute (2 to 5 liters per second) of purge air, which can be readily supplied with instrument air. Maintenance of filters and blowers is thereby completely eliminated. Because our invention is self-aligning, it can be installed on stack surfaces and ductwork that are not especially rigid, without the need for support structure modification or frequent realignment by a technician.

One embodiment of our monitor steers the optical beam using rotating cylindrical prisms. Normally, the control of beam position using these devices is complex because the effect of moving one prism is dependent on the current position of the other prism. However, by tilting the optical assembly, it is possible to create an optical situation in which independent movement of either prism results in movement of the beam in mutually orthogonal directions. This permits use of standard quad detectors and a simple control algorithm.

We further prefer to provide that, in addition to the ability to keep the beam of light centered on a retro-reflector, the mechanism is able to direct the beam in any other desired direction relative to the center of the retro-reflector. By moving the beam to various known angles away from the retro-reflector and then measuring the amount of scattered energy from the beam that nonetheless reaches the retro-reflector, we can create a distribution profile of the light scattered by particulates. The distribution of scattered light is related to the size distribution of the particles, which we then use to calculate the correlation function used to calculate particulate density from the measured opacity.

The ability of the instrument to steer the optical beam also simplifies the zero and upscale calibration checks. Rather than interposing a zero reflector and optical filters into the beam path, our system directs the optical beam onto pre-calibrated surfaces of known reflectivity. Thus, no additional moving parts are required other than those already used to steer the beam. Furthermore, the calibration target is shaped such that, by moving the steered beam slightly, the cross section of the target that is within the beam can be adjusted, thereby eliminating the need for the adjustment iris that is required by the prior art.

Our monitor is useful for measuring particulate concentration, optical transmission or opacity of stacks or ducts for which prior optical light-scattering instruments, such as are used for determination of in benign environments, have not heretofore been successfully applied. Our device can be used to measure corrosive, hot, vibration-prone environments within large utility and industrial stacks and ductwork.

Other objects and advantages of our monitor will become apparent from a description of the certain present preferred embodiments show in the drawings.

DESCRIPTION OF THE PREFERRED EMBODIMENTS

Figure 1:
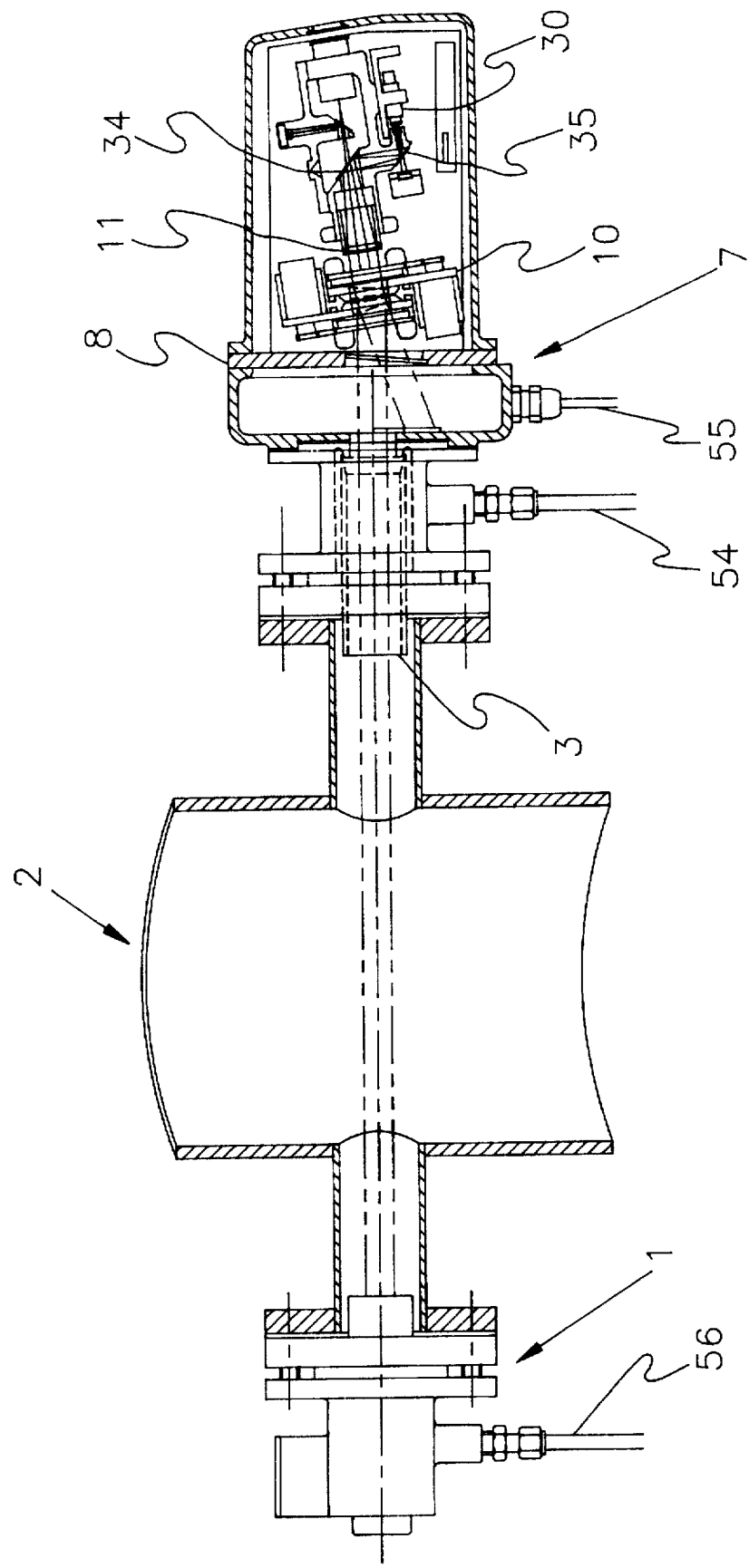
FIG. 1 is a side view partially in section of a present preferred embodiment of our monitor mounted on a portion of a stack or duct.

Referring to FIG. 1, our system has a retro-reflector assembly 1 and an optical assembly or main assembly 7 which are mounted on opposite sides of a conduit 2. This conduit may be a stack or duct containing the gases resulting from burning fossil fuel, or process gases which contain particulates from industrial processes such as, but not limited to waste incineration, lime kilns, petrochemical processes, food processing, and measurement of dust in mine shafts or vehicular tunnels. The conduit 2 illustrated in the drawings is shown to be quite small. This was done only for illustrative purposes as we expect our monitor to be used in conduits ranging in size from a less than a meter to over 40 meters in diameter.

A collimated beam of light is projected from a light source 30 in assembly 7, through the conduit 2 in which the opacity or particulate is to be measured, and to a retro-reflector assembly 1 which returns the beam of light to the optical assembly 7. Retro-reflector assembly 1 also serves the function of providing the optical information used by the beam-steering mechanism 10 within assembly 7. We prefer to use a solid-state laser as the light source. For applications involving measurement of opacity to comply with United States Environmental Protection Agency Regulations, the light source is required to have a peak and mean spectral output between 500 and 600 nanometers. A suitable laser for this application is made by Brimrose, and sold under Model Number BWT-1-E.

Figure 2:
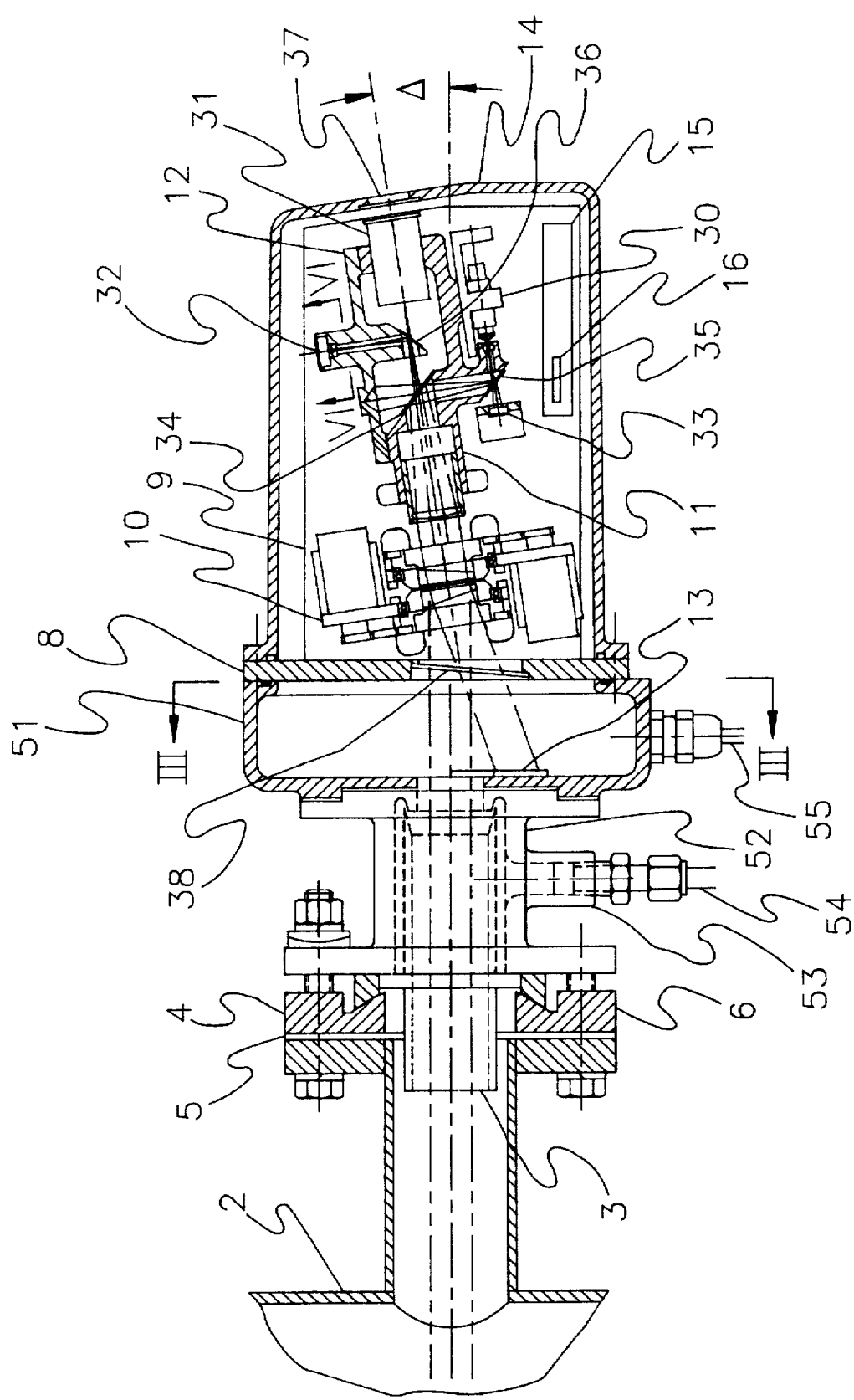
FIG. 2 is a side view partially in section of the optical assembly of the embodiment of FIG. 1.
Figure 6:
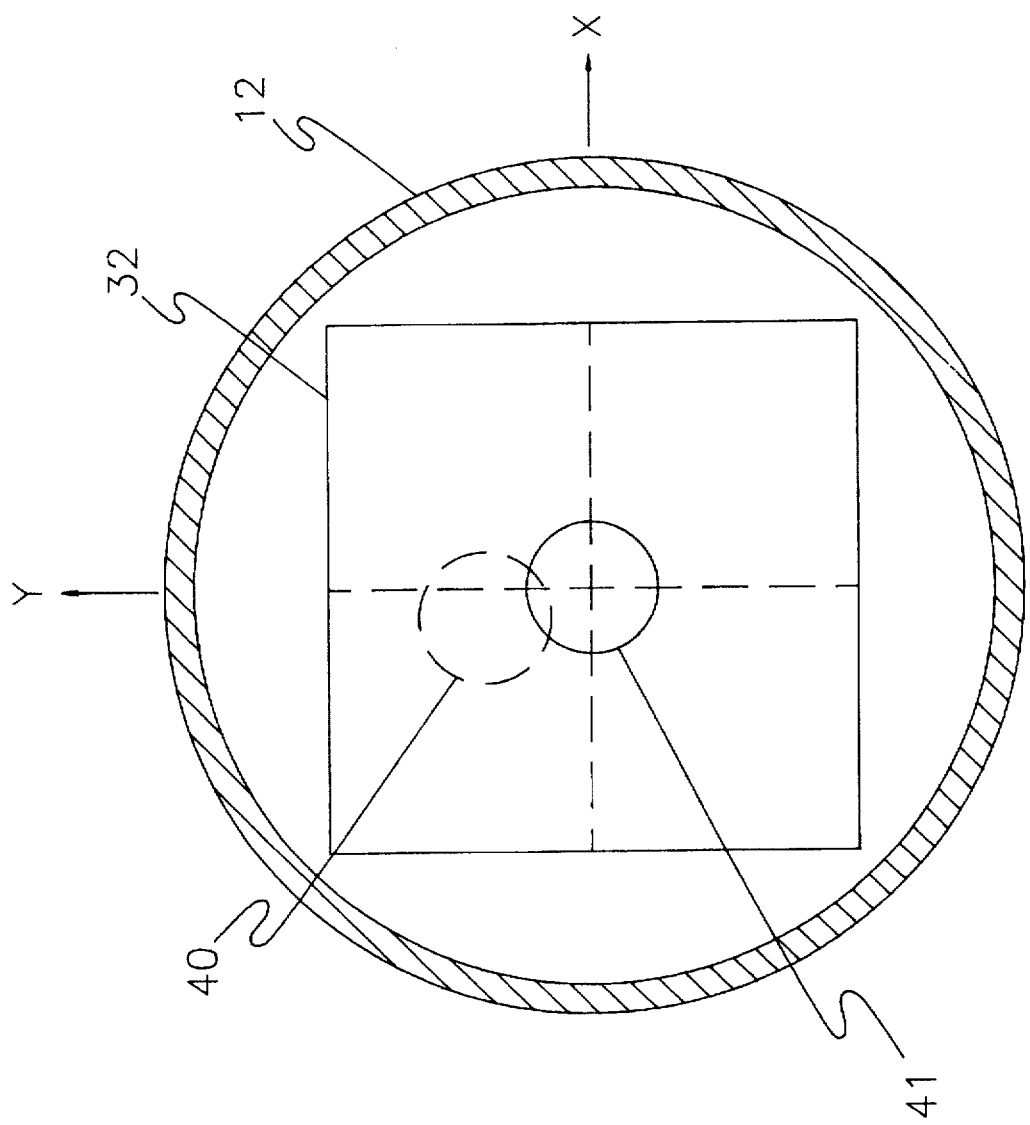
FIG. 6 is a sectional view showing the quad detector that was taken along the line VI—VI in FIG. 2.

FIG. 2 shows the main assembly 7 in more detail. A light beam indicated in chain line from solid state laser 30 is reflected off beam-splitter 35 to second beam-splitter 34, through beam expander 11 and to beam-steering apparatus 10. From the beam-steering apparatus 10, the beam normally traverses the stack 2. We prefer to provide a 0.75" (1.9 cm.) diameter beam coaxially aligned with retro-reflector assembly 1, overfilling a retro-reflector 20, which is 0.25" (0.64 cm.) diameter shown in FIG. 7. Retro-reflector 20 returns the beam through the steering apparatus 10, the beam expander 11 and beam-splitter 34 to beam-splitter 36 which reflects 80% of the beam energy to signal detector 32. Detector 32 preferably is a quad detector able to sense the distribution of the beam on one of four symmetrical detector surfaces. FIG. 6 shows such a situation, in which the projected beam indicated by broken circle 40 is focused onto detector 32 as off-axis, being in the negative x, positive y direction. Separate measurement of position signals from the four elements of quad detector 32 provides feedback signals for control of beam-steering apparatus to bring the focused beam to the desired position 41. Addition of the four signals from the four quadrants of the detector 32 gives information about total attenuation of the beam across the stack, which is a measure of opacity.

Beam-splitter 36 preferably is selected to allow 20% of the beam energy to be focused onto an eyepiece 31, allowing observation of the alignment. The portion of the beam that is transmitted through beam-splitter 35 is focused into reference detector 33 and is used to establish the ratio of the transmitted beam intensity as determined by the total signal from quad detector 32 to the laser intensity as determined by reference detector 33.

Figure 4:
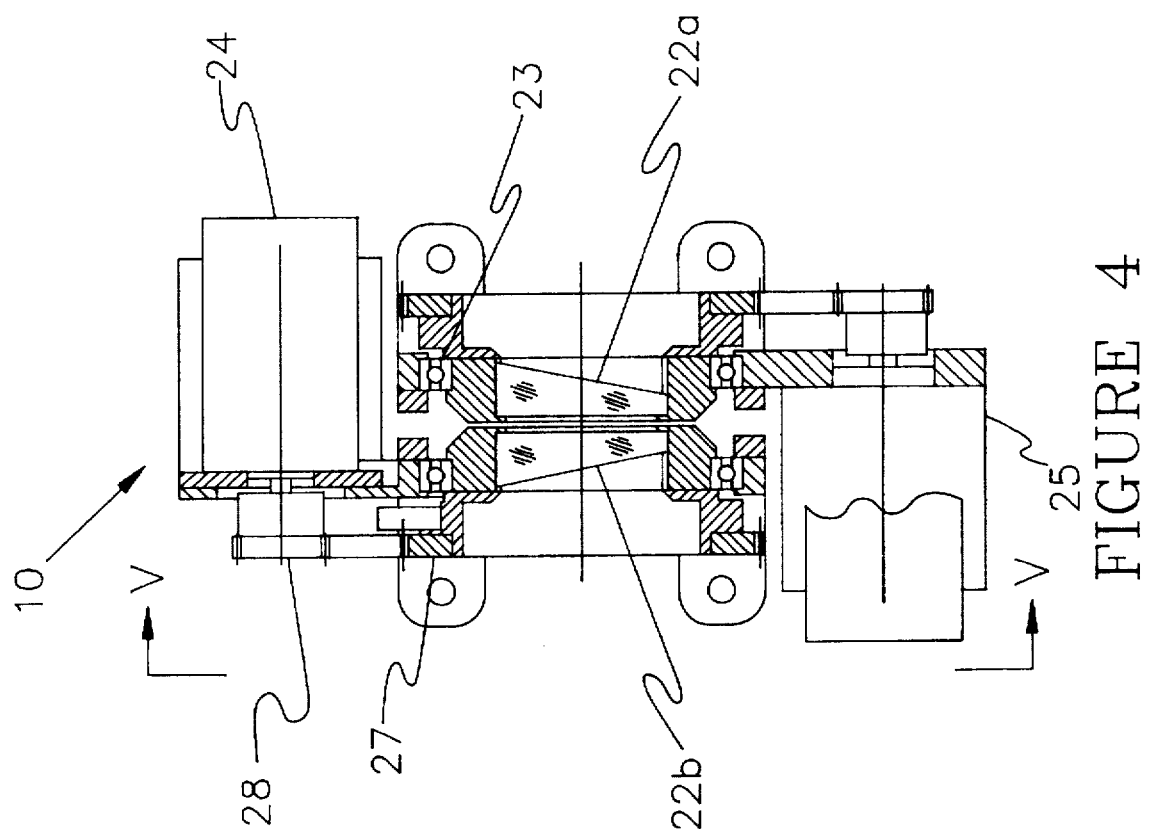
FIG. 4 is a side view partially in section of the beam steering mechanism of the embodiment of FIG. 1.
Figure 5:
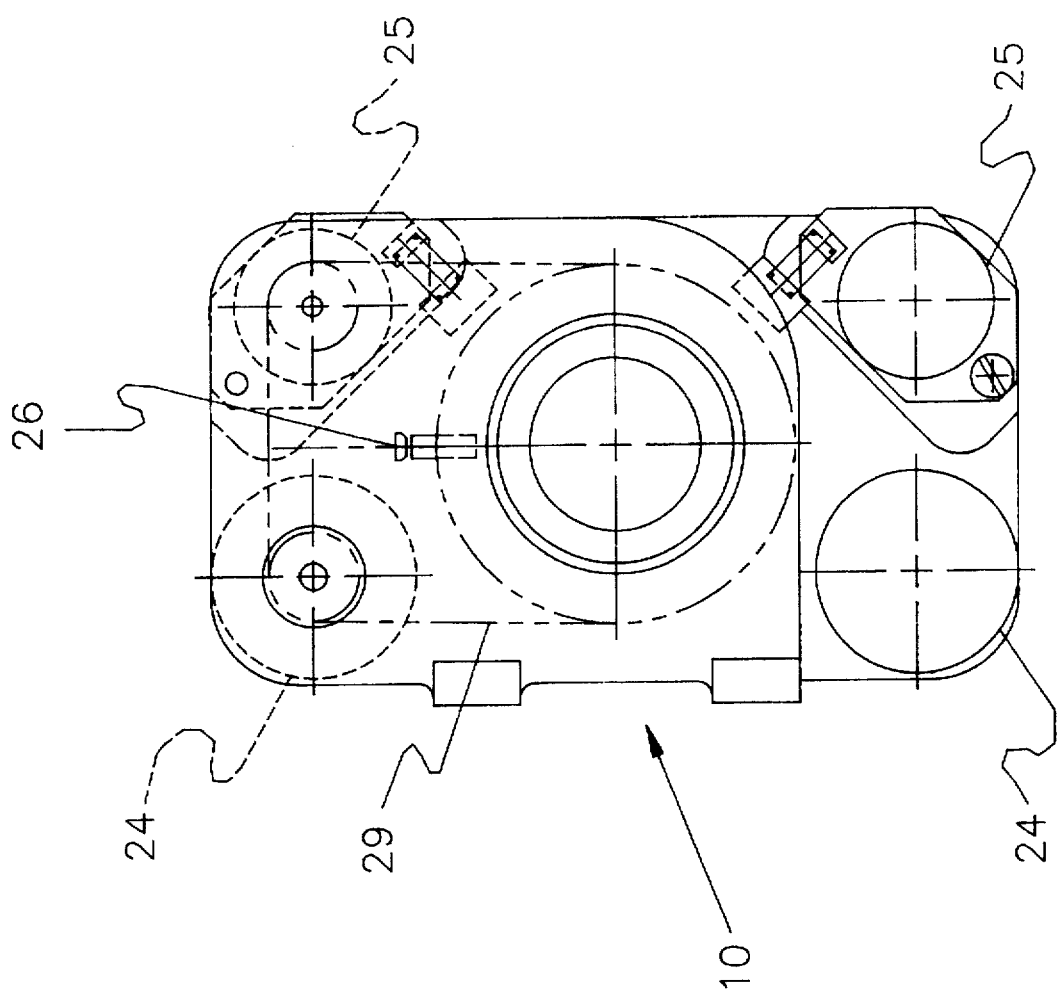
FIG. 5 is an end view of the beam steering mechanism of FIG. 4 taken along the line V—V.

As illustrated in FIGS. 4 and 5, beam-steering apparatus 10 consists of two similar assemblies, each containing one of two wedge prisms 22a and 22b. Each prism is axially aligned with beam expander 11. As can be seen is FIG. 5, there is a servo motor 24, timing belt 29 and encoder 25 associated with each prism. Each prism can be independently rotated via bearings 23, timing belt 29 driven by servo motor 24 and encoder 25 Each prism is associated with a homing switch 26 which is used as a reference point for the encoder 25. Homing switch 26 is activated once per revolution of the associated prism 22a or 22b. Each encoder is related to a prism via a 4:1 gear ratio such that the encoder rotates 4 times per prism rotation. Each encoder 25 has three square-wave outputs: (1) a once-per-encoder pulse, (2) a 0°-phase pulse for each 0.18 degrees of rotation of the encoder, and (3) a 90°-phase pulse, that lags the 0°-phase pulse by a quarter-cycle, for each 0.18 degrees of rotation of the encoder. The 0° and 90° phase pulses indicate which direction the encoder is turning. The encoder resolution, combined with the 4:1 gear ratio, enables the system to know the rotation of the prisms by ±0.045°.

We prefer to use wedge prisms which are able to cause a deflection of 6° in the direction of the beam passing through it. Rotating either prism about 360° causes the expanded laser beam to describe a circle corresponding to a 6° deflection of the beam. By independently controlling the motion of the two prisms, the beam can be steered to any direction inside a 12° deviation from its original direction. Since the system can identify prism rotation to within ±0.045°, and since a 180° prism rotation creates a change of direction of 6° in the projected beam, it follows that we are able to identify the beam direction to within ±(0.045/180) (6°)=±0.0015°. At a distance of 130 feet, or about 40 meters, this corresponds to a beam deflection of (130 feet)tan (±0.0015°)=±0.034 inches or ±0.086 cm. This is more than adequate resolution for maintaining the beam onto the retro-reflector.

Figure 8:
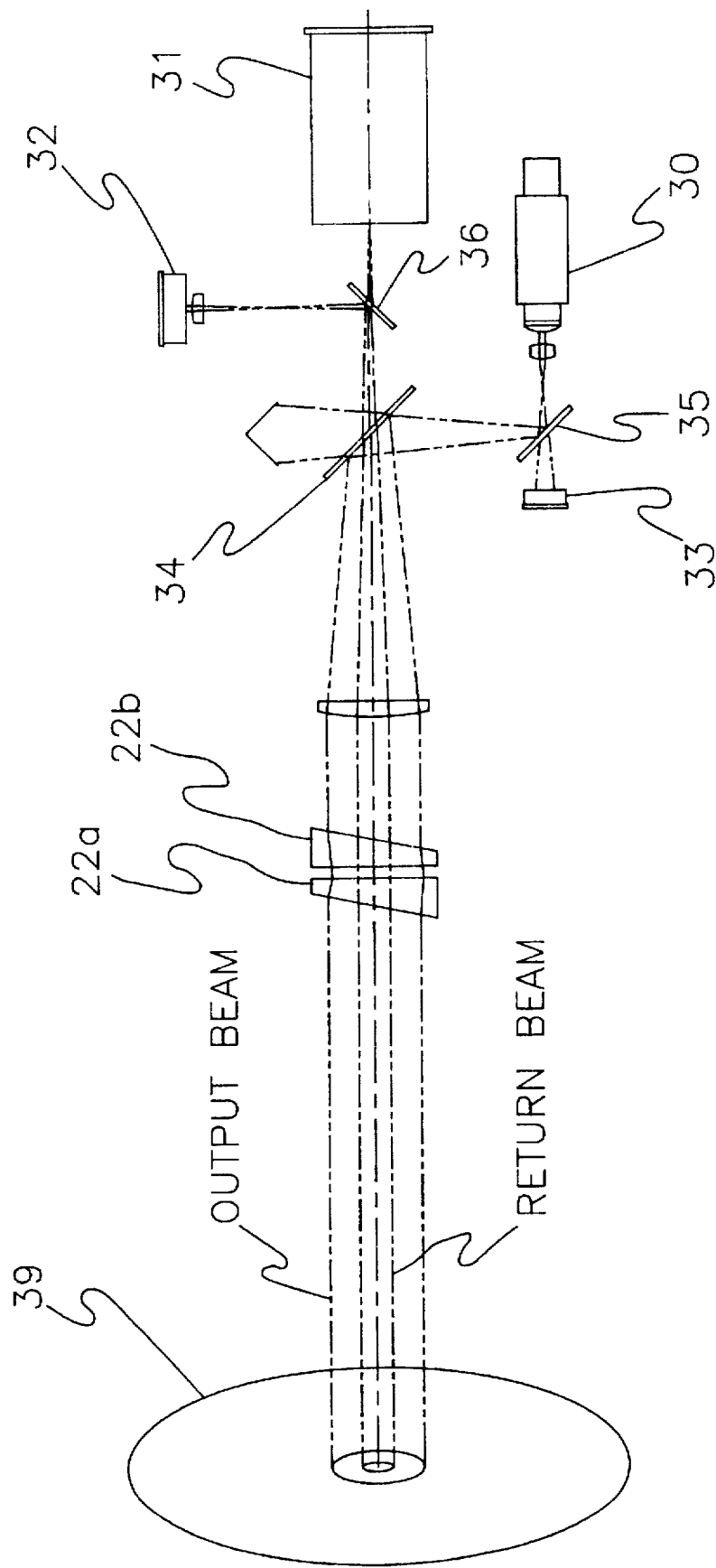
FIG. 8 is an optical diagram showing the light path which the beam steering mechanism is in a zero position.
Figure 9:
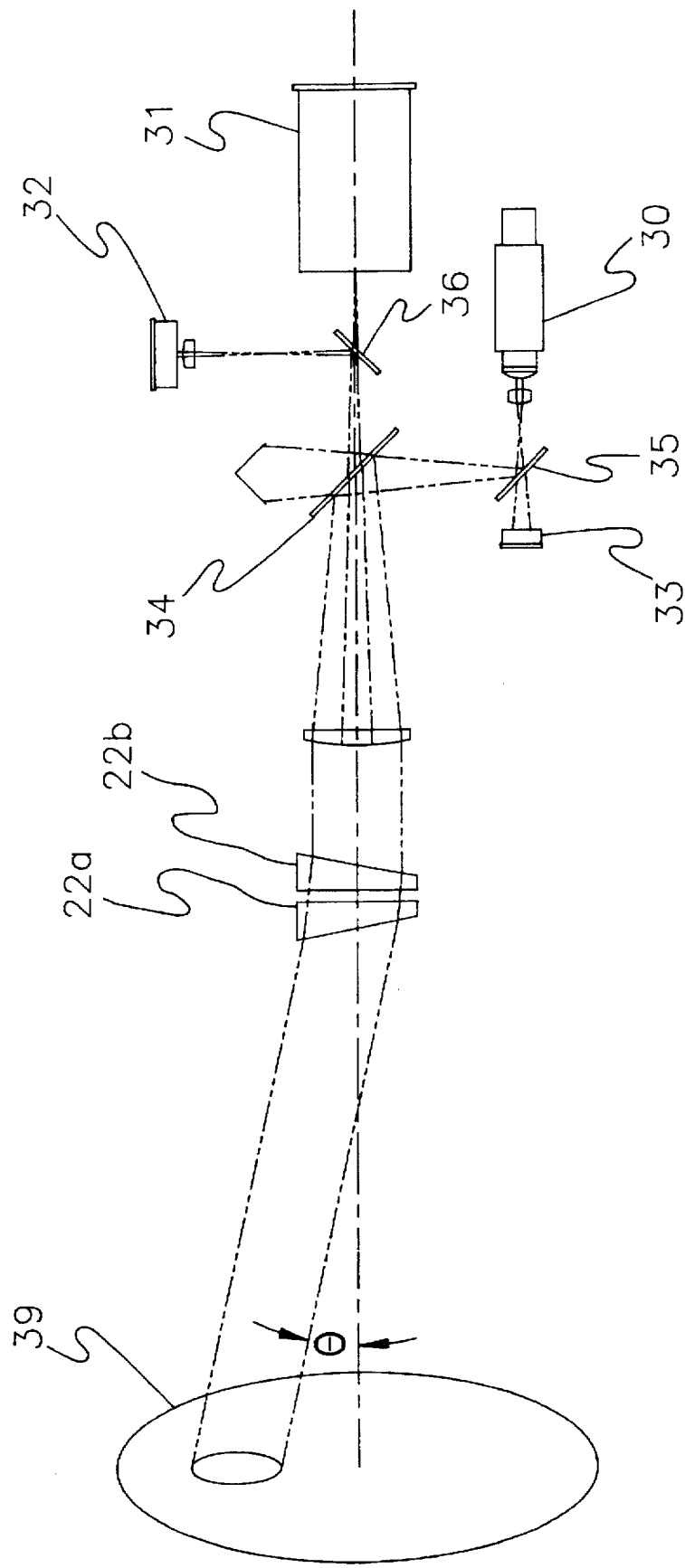
FIG. 9 is an optical diagram similar to FIG. 8 showing the light path which the beam steering mechanism is in a full up position.
Figure 10:
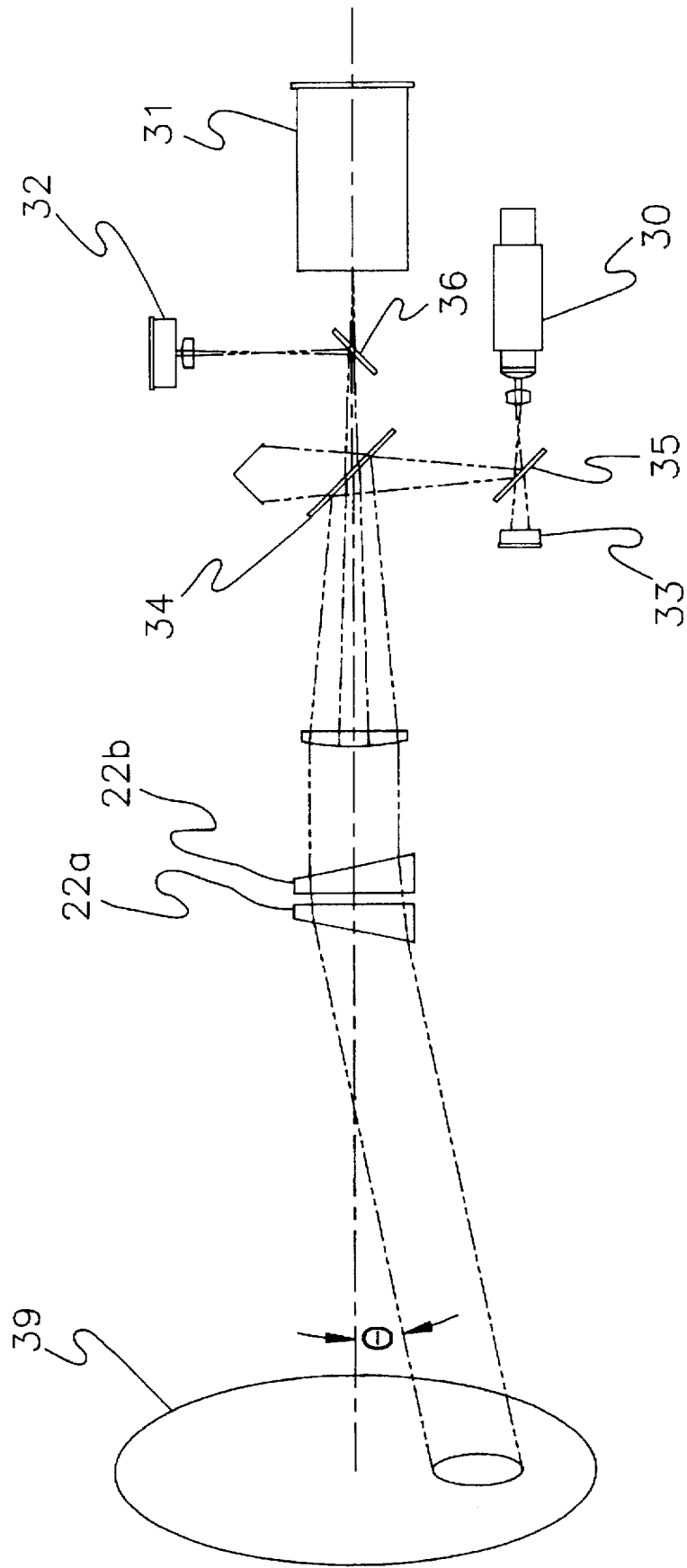
FIG. 10 is an optical diagram similar to FIG. 8 showing the light path which the beam steering mechanism is in a full down position.

FIG. 8 shows the situation in which the prisms are anti-aligned so as to produce no change in the direction of the beam. This is referred to as the Home Position of the beam. FIG. 9 shows the situation in which the two prisms are aligned with the thick edges of the prisms vertically aligned upward. We call this the Full Up direction of the beam which strikes surface 39 on the retro-reflector assembly or stack wall. When wedge prisms are used that create a deflection of 6° angle Θ will be 12° above the optical axis. FIG. 10 shows the situation in which the two prisms are aligned with the thick edges of the prisms vertically aligned downward. We call this is the Full Down direction of the beam. When wedge prisms are used that create a deflection of 6° angle Θ will be 12° down from the optical axis.

If, from the Full Up position of FIG. 9, the two prisms are rotated in opposite directions, one clockwise and one counter-clockwise, by 45°, it is straightforward trigonometry to show that the beam will be steered to a direction 8.5° vertically above the Home Position. It is also apparent that, because the thick side of each prism is now at a 45° angle with respect to the vertical and horizontal planes, that a small rotations of either prism, with the other held stationary, will produce a movement in the projected beam that is at approximately a 45° angle with respect to the vertical and horizontal planes. The effect of individual moving Prism 22a will, in addition, be orthogonal to the effect of moving prism 22b. Referring again to FIG. 6, the quad detector 32 can be oriented within the optical system such that the detector's x-axis is predominately associated with movements of prism 22a while the detector's y-axis is predominately associated with movements of prism 22b. This makes possible the development of simpler control algorithms in the region of 8.5° beam direction than is possible in the near-region of other beam directions.

As shown in FIGS. 1 and 2, we prefer that the entire apparatus of laser, beam expander, steering apparatus, detectors and beam-splitters be tilted downward at an angle $\Delta$ of 8.5° with respect to the axis formed by the center of the front window 38 and retro-reflector 20 in the retro-reflector assembly 1. This results in a configuration such that when the beam is pointing out of the ±1° cone angle defined by the mounting nozzle 3, prisms 22a and 22b will be oriented such that the mutually orthogonal effect of individual rotations will apply.

As seen most clearly in FIG. 2, the laser, beam-splitters, beam expander and detectors are affixed to an optical bench 12 that preferably is a precision casting. The components, along with the beam-steering apparatus 10, are affixed to a base-plate 9 mounted on a plate 8 which also contains the front window 38. Intermediate housing 51 provides access to a calibration target to be described later. Purge housing 52 includes provision for a purge port 53 connected to nozzle 3 which provide protection of the window 38 and calibration target 13 from heat and gases. Purge air is supplied through line 54 that preferably is connected to a source of dry, filtered, instrument air. The overall apparatus is designed so that the optical assembly 7 and the retro-reflector assembly 1 each fit onto a system flange 4 which contacts a seal 5. The beam steering assembly is preferably controlled by a microprocessor (not shown) positioned within the optical assembly. Power and communication lines (not shown) for the microprocessor, motors, encoders light source and detectors are provided through conduits 55. Purge air for the retro-reflector is provided through conduit 56. The entire assembly is protected from rain, dust and other factors by a cover 14, having a window 37 opposite eyepiece 31.

Figure 3:
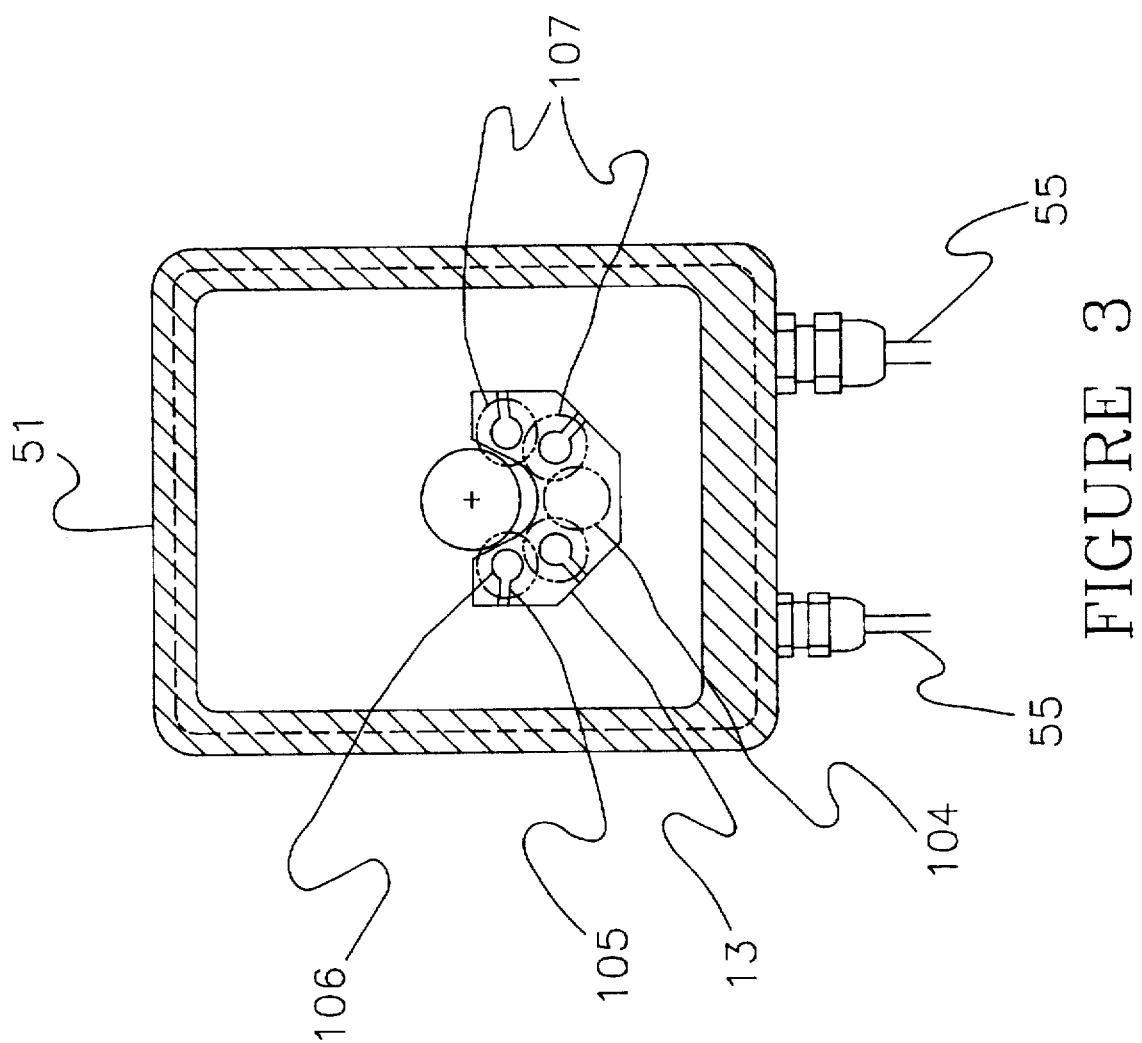
FIG. 3 is a sectional view taken along the line III—III of FIG. 2.

FIG. 3 is an inboard view of the intermediate housing 51. The calibration target as depicted shows in chain line alternate positions of the beam 107 as a 1.5" projected spot which may be steered to one of five locations on the target. One of the five locations is a flat black or other absorbing surface 104 which serves to simulate the situation of 100% opacity in the conduit, or infinitely high particulate loading in the conduit which does not permit any of the beam to cross the conduit. Each of the other four calibration targets includes a reflective disc 106 and reflective rectangle 105 which, when co-illumninated by the beam, reflect back an amount of energy approximately equal to the energy that would be reflected from retro-reflector 20 under clear-conduit conditions. By adjusting the steering of the beam to include more or less of reflective rectangle 105, the equivalency of the calibration target and cross-conduit retro-reflector 20 can be achieved with any desired degree of accuracy. This feature of our invention eliminates the need for mechanical adjustment of a calibration iris. A linearity check, to any desired upscale opacity, can be achieved by affixing neutral density filters of known optical transmission, to calibration targets.

As shown in FIG. 3, the centers of the four reflective discs 106, as well as the centerlines of the four reflective rectangles 105 are arranged symmetrically about the Home Position of the beam. This means that, once the prism positioning needed to establish equivalency with retro-reflector 20 is established the other four calibration locations can be located by the simple procedure of rotating both prisms by a number of degrees equivalent to the angular separation of the targets from the home position.

Figure 7:
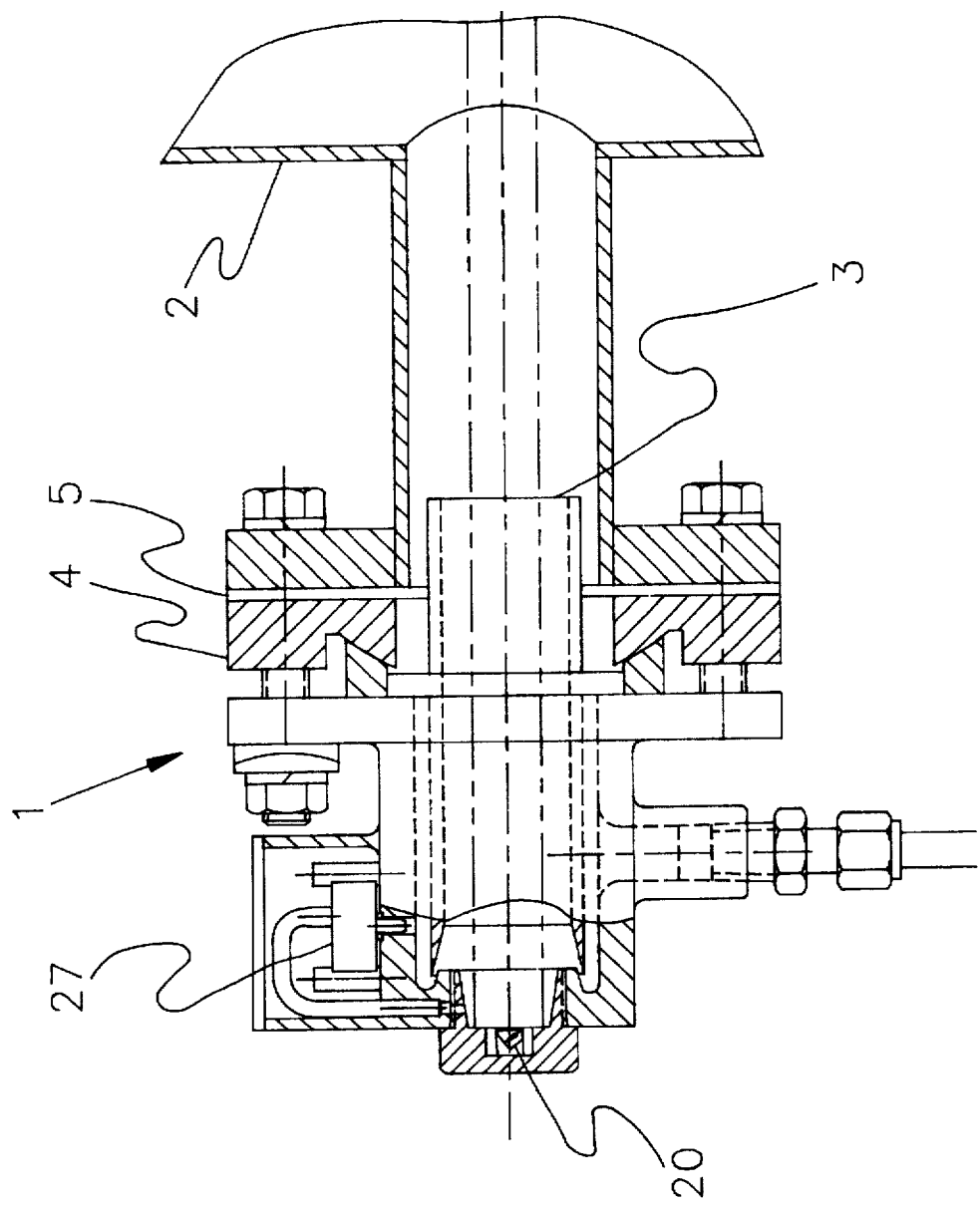
FIG. 7 is a side view partially in section of the retro-reflector assembly of the embodiment of FIG. 1.

Additional details of the retro-reflector assembly 1 are shown as FIG. 7. Flange 4, seal 5, and purge nozzle 3 are equivalent to those in FIG. 2. A purge air sensing switch 27 is shown monitoring the pressure drop across the purge venturi.

Figure 11:
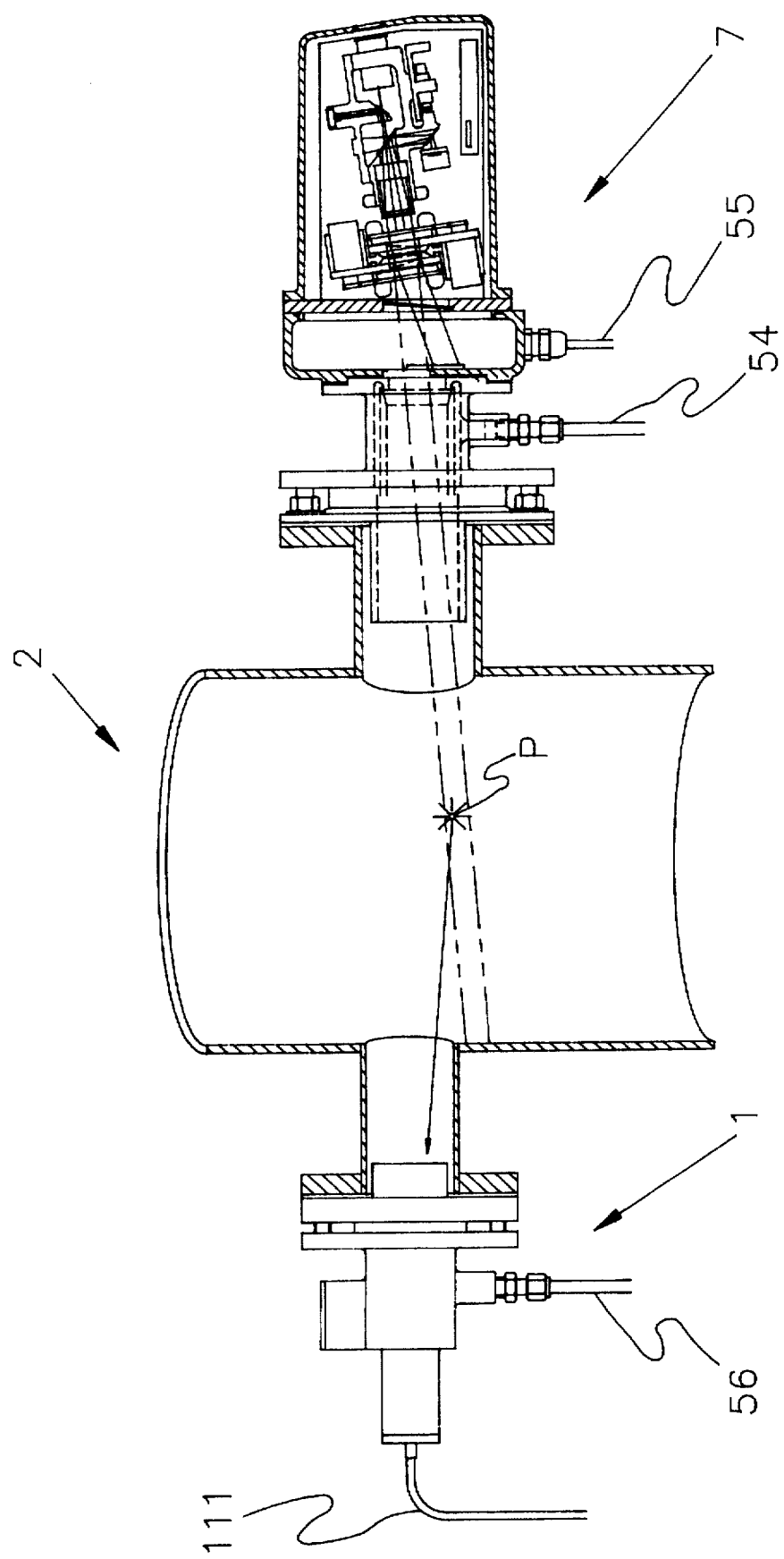
FIG. 11 is a side view partially in section of a second present preferred embodiment of our monitor mounted on a portion of a stack or duct.

Evaluation of the opacity caused by particulate in the stack provides only partial information about particulate concentrations. Additional information is achieved by measuring and evaluating the angular distribution of light scattered from the beam. This can be done by the second preferred embodiment of our monitor shown in FIGS. 11, 12 and 13. FIG. 11 depicts the situation in which the system first aligned the beam across the stack by using signals from the quad detector 32 to enable the beam-steering apparatus 10 to center the beam on and about retro-reflector 20. Both opacity and near-forward scattered light can be measured in this configuration. The beam steering apparatus 10 now uses information from the encoder 25 to point the beam at one of a number of desired angles such that no energy from the primary 1.5" beam is entering nozzle 3. The only optical energy entering nozzle 3 will be due to scattered light from particulates in the conduit 2 as indicated by particle P in FIG. 11. Note that the size of purge nozzle 3 on the source side of the conduit is made larger to enable larger steered angles to be achieved. Preferably angles of from 0° to 6° will be used.

Figure 12:
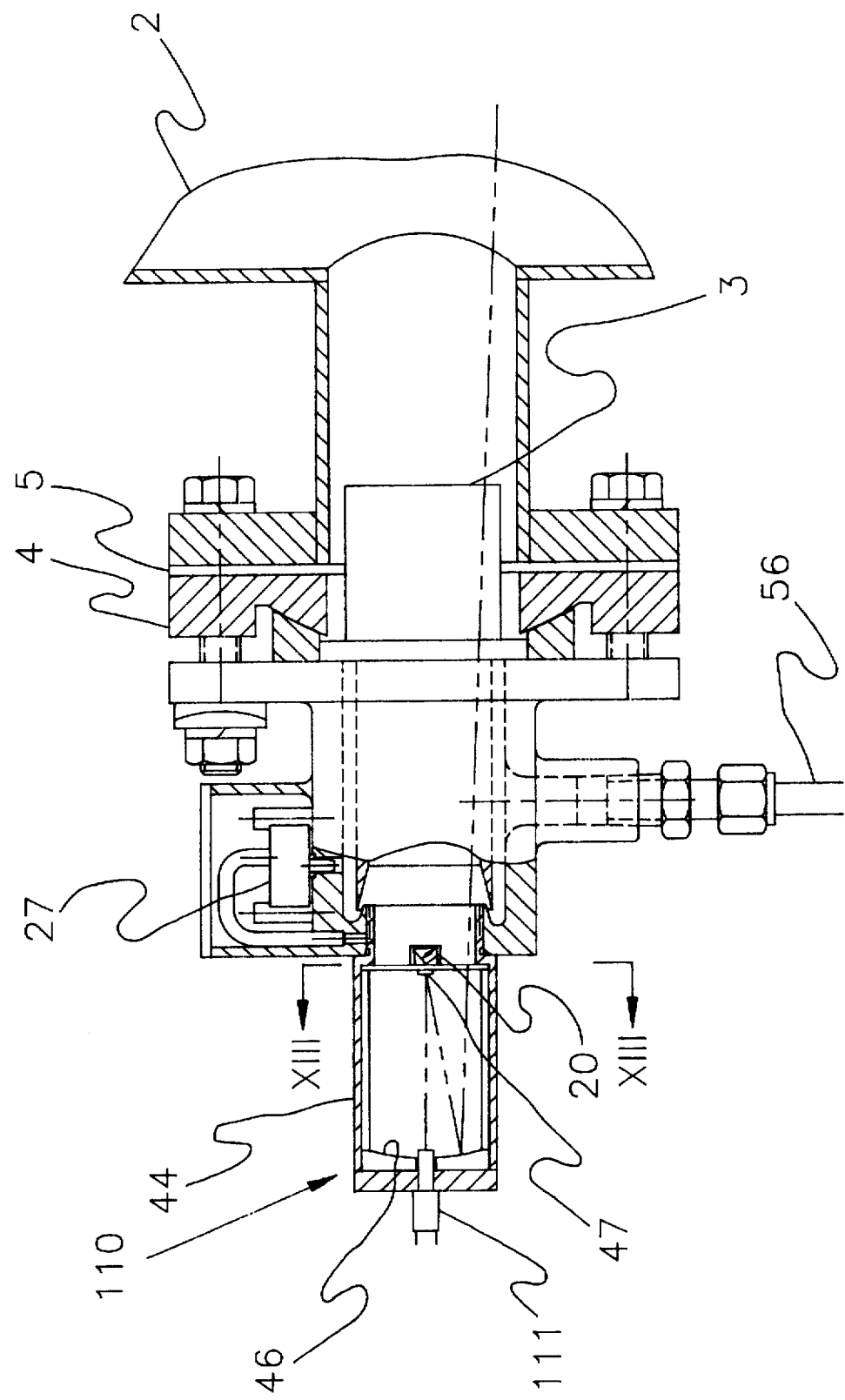
FIG. 12 is a side view partially in section of the retro-reflector assembly of the embodiment of FIG. 11.
Figure 13:
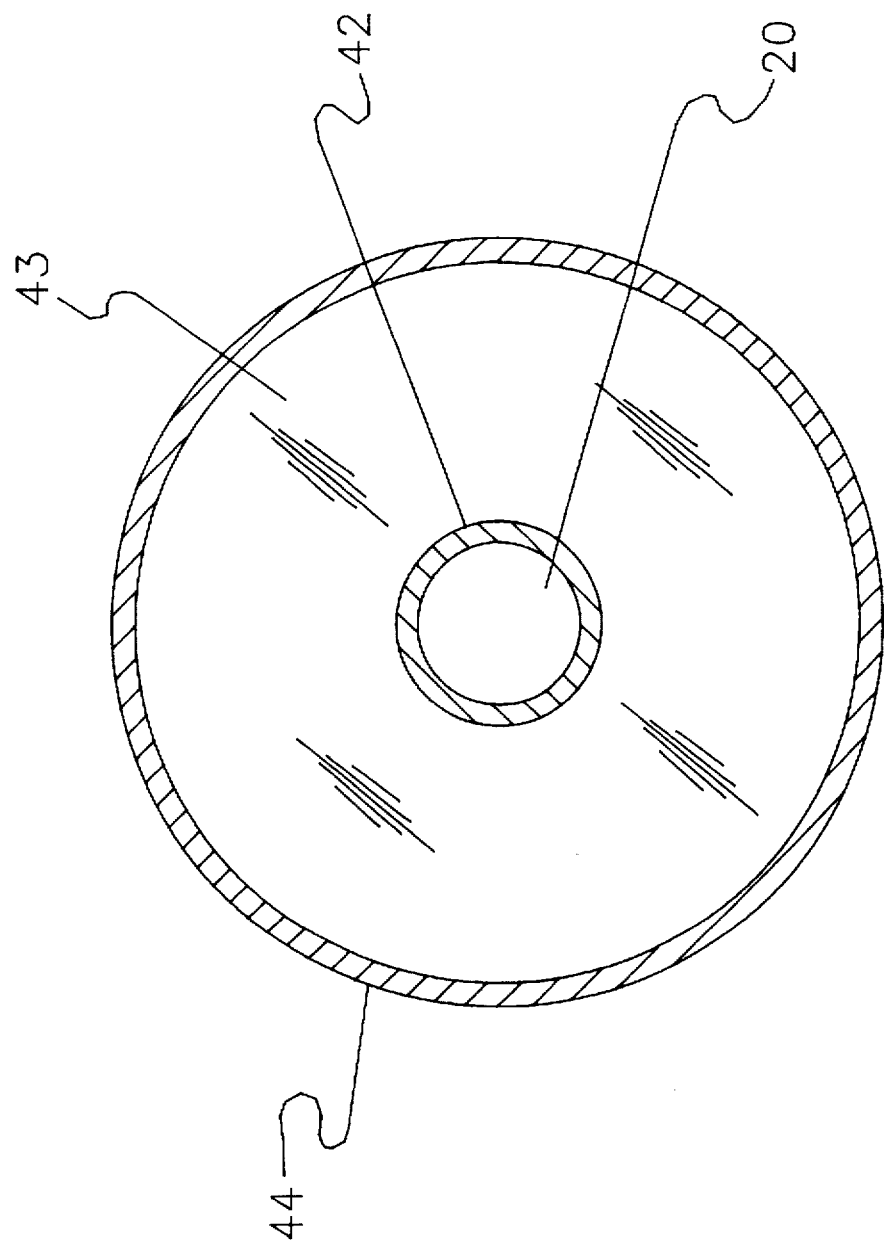
FIG. 13 is a sectional view taken along the line XIII—XIII in FIG. 12.

The details of how the scattered light is measured can be understood from FIGS. 12 and 13. Retro-reflector 20 is carried in a housing 42 that is bonded to the center of a glass plate 43. When the diameter of the light beam from the solid state light source is larger than the retro-reflector or that beam is directed to a position adjacent housing 42 light will enter into a Cassegrain Telescope 110. That light will strike primary mirror 46 and be reflected to secondary mirror 47 located behind the retro-reflector 20. This folded annular beam of scattered energy is thereby focused onto one end of fiber optical cable 111. The other end of cable 111 is connected to an analyzer (not shown) where the information is processed, preferably by the same microprocessor circuitry as is used for the opacity measurement. This information, taken over scattering angles of from 0° to 6°, permits more accuracy of the correlation of opacity to actual mass loading of particulates. If desired, quad detector 32 could be used to detect backscattered light from the same particle P. This will, in some cases, necessitate installation of a light trap at the location where the beam strikes the far wall of the conduit.

We prefer to provide electronic and microprocessor components and software programs in the electronic module 15, shown in FIG. 2, to provide automatic alignment, to enable the system to re-establish alignment following power failures, and to provide means for automatic checks of system calibration without the need of moving parts other than the beam-steering mechanism. Electronic module 15 includes a drive controller 16 which can be used to operate the laser 30 in a pulsed mode so as to reduce the fraction of time that the laser 30 is operating so as to extend laser life. In typical operation for opacity monitoring or light-scattering measurements, the laser is operated in a 50% duty modulation mode for 200 milliseconds out of every second, for an effective duty of 10%, while providing a useful signal as a light beam for applications only requiring response times of a few seconds.

Although we have shown and described certain present preferred embodiments of our monitor it should be distinctly understood that our invention is not limited thereto but may be variously embodied within the scope of the following claims.

We claim:

1. A monitor comprised of:
   a. a housing sized and configured for attachment to a conduit and having a window through which light may pass;
   b. a solid state light source within the housing;
   c. a beam steering unit within the housing and having a pair of colinear rotatable wedge prisms positioned to direct a light beam from the light source through the window and across the conduit; and
   d. at least one detector positioned to receive the light beam from the solid state light source after that light beam has passed through the conduit and to receive light which has been forward scattered after striking particles in the conduit which detector produces a signal corresponding to intensity of light received by the detector the signal being useful for measuring at least one of opacity of a medium passing through the conduit and light scattered by particulates in the conduit.

2. The monitor of claim 1 also comprising a reference detector positioned within the housing to receive a reference light beam from the solid state light source.

3. The monitor of claim 2 also comprising a beam splitter positioned within the housing for splitting a beam from the solid state light source into a reference beam and a measuring beam and directing the measuring beam through the conduit and the reference beam to the reference detector.

4. The monitor of claim 2 wherein the at least one detector is a quad position detector and electronically connected to the reference detector and the beam steering unit.

5. The monitor of claim 1 wherein the detector is within the housing and also comprising a retro-reflector positioned to reflect back through the conduit to the detector a light beam from the solid state light source which has passed through the conduit.

6. The monitor of claim 5 also comprising a second signal detector and a beam splitter positioned to split the beam which has passed through the conduit into a first beam directed to the second signal detector and second beam directed to the at least one detector.

7. The monitor of claim 5 also comprising detection optics positioned near the retro-reflector which detection optics can detect scattered light from the light beam when the light beam is aimed at a known angle relative to the detection optics.

8. The monitor of claim 7 wherein the detection optics comprise a Cassegrain telescope.

9. The monitor of claim 8 also comprising a fiber optic cable connected between the Cassegrain telescope and the housing.

10. The monitor of claim 5 wherein the beam steering unit is comprised of a pair of rotatable wedge prisms in an optical path of the light beam such that the light beam is directed to the retro-reflector when the prisms are orthogonal to one another, as a result of which independent motion of either prism will cause orthogonal movement of the light beam from the solid state light source.

11. The monitor of claim 1 wherein the beam steering unit also comprises a first servo motor connected to rotate one wedge prism and a second servo motor connected to rotate the other wedge prism.

12. The monitor of claim 11 wherein the beam steering unit also comprises a first encoder connected to the first wedge prism and a second encoder connected to the second wedge prism.

13. The monitor of claim 1 also comprising a calibration assembly having at least one region of a known reflectivity which assembly is positioned within the housing so that the beam steering unit directs a light beam onto the at least one region for reflection to the detector.

14. The monitor of claim 1 wherein the solid state light source is a laser.

15. The monitor of claim 14 also comprising a drive controller attached to the laser for turning the laser on and off in a sequence which will provide a useful light beam for at least one of opacity monitoring and forward scatter monitoring thereby providing reduced duty operation for extended laser life.

16. The monitor of claim 1 wherein the solid state light source has peak and mean spectral response between 500 and 600 nanometers.

17. A monitor comprised of:
   a. housing sized and configured for attachment to a conduit and having a window through which light may pass;
   b. a solid state light source within the housing;
   c. a beam steering means within the housing and positioned for directing a light beam from the light source through the window and across the conduit; and
   d. at least one detecting means positioned for receiving the light beam from the solid state light source after that light beam has passed through the conduit and for receiving light which has been forward scattered after striking particles in the conduit which detector produces a signal corresponding to intensity of light received by the detector the signal being useful for measuring at least one of opacity of a medium passing through the conduit and light scattered by particulates in the conduit.

18. The monitor of claim 17 wherein the detecting means is within the housing and also comprising retro-reflecting means for reflecting back through the conduit to the detecting means a light beam from the solid state light source which has passed through the conduit.

19. The monitor of claim 18 also comprising detection optic means positioned near the retro-reflecting means which detection optic means can detect scattered light from the light beam when the light beam is aimed at a known angle relative to the detection optic means.

* * * * *

UNITED STATES PATENT AND TRADEMARK OFFICE
CERTIFICATE OF CORRECTION

PATENT NO. : 5,751,423
DATED : May 12, 1998
INVENTOR(S) : John E. Traina, Richard Myers, Edward A. Smierciak It is certified that error appears in the above-indentified patent and that said Letters Patent is hereby corrected as shown below:

On the title page:

At [56] References Cited, please add the following patents and publications:

3,797,937 3/74 Shofner 356/102
4,017,186 4/77 Shofner 356/103
Catalogue of Durag Industrie Elektronik entitled "D-R 300" dated January, 1993
Catalogue of Durag Industrie Elektronik entitled "Line of Products" dated January, 1993
Catalogue of Environmental Systems Corporation entitled "Particulate Monitor Model P-5A", no date available Signed and Sealed this Twenty-sixth Day of January, 1999

Attest:

Attesting Officer

*Acting Commissioner of Patents and Trademarks*